(12) United States Patent
Boschetti et al.

(10) Patent No.: US 8,021,889 B2
(45) Date of Patent: Sep. 20, 2011

(54) CHROMATOGRAPHIC MATERIAL FOR THE ABSORPTION OF PROTEINS AT PHYSIOLOGICAL IONIC STRENGTH

(75) Inventors: Egisto Boschetti, Croissy sur Seine (FR); Pierre Girot, Paris (FR)

(73) Assignee: Pall Corporation, Port Washington, NY (US)

( * ) Notice: Subject to any disclaimer, the term of this patent is extended or adjusted under 35 U.S.C. 154(b) by 1496 days.

(21) Appl. No.: 10/583,509

(22) PCT Filed: Jan. 14, 2005

(86) PCT No.: PCT/US2005/001304
§ 371 (c)(1), (2), (4) Date: Jun. 16, 2006

(87) PCT Pub. No.: WO2005/073711
PCT Pub. Date: Aug. 11, 2005

(65) Prior Publication Data
US 2007/0151910 A1    Jul. 5, 2007

Related U.S. Application Data

(60) Provisional application No. 60/537,342, filed on Jan. 20, 2004.

(51) Int. Cl.
*G01N 30/00* (2006.01)
*B01D 15/08* (2006.01)
*C07C 7/12* (2006.01)

(52) U.S. Cl. .......... 436/161; 436/62; 435/803; 210/656; 585/825

(58) Field of Classification Search .................. None
See application file for complete search history.

(56) References Cited

U.S. PATENT DOCUMENTS

| | | |
|---|---|---|
| 3,917,527 A | 11/1975 | Shaltiel |
| 4,696,980 A | 9/1987 | Porath |
| 5,075,371 A | 12/1991 | Boschetti et al. |
| 5,234,991 A | 8/1993 | Tayot et al. |
| 5,268,097 A | 12/1993 | Girot et al. |
| 5,641,870 A | 6/1997 | Rinderknecht et al. |
| 5,719,060 A | 2/1998 | Hutchens et al. |
| 5,789,578 A | 8/1998 | Burton et al. |
| 5,945,520 A | 8/1999 | Burton et al. |
| 6,124,137 A | 9/2000 | Hutchens et al. |
| 6,225,047 B1 | 5/2001 | Hutchens et al. |
| 6,413,920 B1 * | 7/2002 | Bettiol et al. ............. 510/101 |
| 2004/0124149 A1 | 7/2004 | Boschetti et al. |
| 2004/0214157 A1 | 10/2004 | Burton et al. |

FOREIGN PATENT DOCUMENTS

| | | |
|---|---|---|
| EP | 0 165 912 | 12/1985 |
| EP | 0 180 563 | 5/1986 |
| GB | 2 230 010 | 10/1990 |
| JP | 10-502339 | 3/1998 |
| JP | 10-506987 | 7/1998 |
| JP | 2000502951 | 3/2000 |
| WO | WO 92/16292 | 10/1992 |
| WO | WO 96/00735 | 1/1996 |
| WO | WO 03/064594 | 8/2003 |
| WO | WO 2004/024318 | 3/2004 |
| WO | WO 2006/043896 | 4/2006 |

OTHER PUBLICATIONS

Gemeiner et al. Cellulose as a (bio)affinity carrier: properties, design and applications. Journal of Chromatography B 1998, vol. 715, pp. 245-271.*
B.-L. Johansson et al., *J. Chromatography A*, 1016: 21-33 (2003).
B.-L. Johansson et al., *J. Chromatography A*, 1016:35-49 (2003).
S. C. Burton et al., *J. Chromatograph A*, 814:71-81 (1998).
L. Guerrier et al., Bioseparation, 9:211-221 (2000).
G. H. Scholz et al., *J. Chromatography B: Biomedical Sciences and Applications*, 709:189-196 (1998).
International Preliminary Examination Report on Patentability for PCT/US2005/001304 mailed Aug. 3, 2006.

* cited by examiner

*Primary Examiner* — Shafiqul Haq
(74) *Attorney, Agent, or Firm* — Leydig, Voit & Mayer, Ltd.

(57) ABSTRACT

Ion exchange and hydrophobic interaction chromatographic materials are constructed by tethering a terminal binding functionality to a solid support via a hydrophobic linker. The backbone of the linker typically comprises sulfur-containing moieties. Suitable terminal binding functionalities are tertiary amines, quaternary ammonium salts, or hydrophobic groups. These chromatographic materials possess both hydrophobic and ionic character under the conditions prescribed for their use. The separation of proteins from crude mixtures at physiological ionic strength can be accomplished with a chromatographic material of this type by applying pH or ionic strength gradients, thereby effecting protein adsorption and desorption.

7 Claims, No Drawings

CHROMATOGRAPHIC MATERIAL FOR THE ABSORPTION OF PROTEINS AT PHYSIOLOGICAL IONIC STRENGTH

BACKGROUND OF THE INVENTION

The present invention relates generally to the field of ion exchange and hydrophobic interaction chromatographic materials in the context of separation science and analytical biochemistry.

The increasing need for bulk quantities of biologically relevant molecules (i.e., biomolecules) such as proteins has spawned a variety of techniques for isolating such biomolecules from physiological isolates. Traditional techniques in this regard include precipitation methods, electrophoretic separations, and membrane filtration. One of the more promising separation methodologies advanced, however, is liquid chromatography.

Chromatographic separations of complex biomolecules typically require one or more modifications of the sample that contains the biomolecules. The interactions between biomolecules and a chromatographic sorbent include electrostatic attraction and repulsion, ion exchange, hydrophobic associations, charge transfer, and van der Waals attraction. These forces often compete with each other to impose a delicate balance between conditions that are suitable for a biomolecule to adsorb onto a chromatographic sorbent and those conditions under which the biomolecule may desorb. Crude physiological isolates, such as whole blood, exhibit non-ideal pH and ionic strength, for example, for desired proteins to adsorb to typical sorbents. As a consequence of these interactions, it is necessary to adjust the pH and/or ionic strength of physiological samples to achieve biomolecule adsorption. It may be additionally necessary to add chemical additives or to dilute or concentrate the samples prior to chromatographic separations.

A useful subset of chromatographic resins that are subject to these limitations are ion exchange resins, which primarily attract biomolecules such as proteins via opposing charges on the resins and proteins. In this regard, typical ion exchange resins adsorb proteins at pH 4 to 10 and at low to very low ionic strength. The pH of a sample containing a protein dictates the net charge of the protein, which, of course, must be opposite to the charge of the chromatographic resin. Thus, crude biological samples must be adjusted to higher or lower pH as a prerequisite to confer net charges for protein separations.

Achieving the correct pH of a sample is not always sufficient to promote the adsorption of a protein to an ion exchange resin. The ionic strength of a sample exerts a powerful influence on adsorption since the counterions that are present in the form of salts can compete with the protein charges for the charged resin. If the ionic strength of a sample is too high, then proteins will not adsorb to the resin. The physiological ionic strength of most biological extracts are 15-20 mS/cm, whereas most chromatographic separation conditions require the ionic strength to be between about 1 mS/cm and 10 mS/cm. Johansson et al., for example, describe a number of multi-modal ligands that feature primary or secondary amines as anion-exchange groups, or certain carboxylic acids as cation exchange groups, for the adsorption of biomolecules. However, these ligands require high ionic strength for biomolecule adsorption. See B. L. Johansson et al. "Preparation and Characterization of Prototypes for Multi-Modal Separation Media Aimed for Capture of Negatively Charged Biomolecules at High Salt Conditions," 814 *J. Chromatography A* 71-81 (1998) and B. L. Johansson et al. "Preparation and Characterization of Prototypes for Multi-Modal Separation Aimed for Capture of Positively Charged Biomolecules at High Salt Conditions," 1016 *J. Chromatography A* 35-49 (2003).

Another useful subset of chromatographic resins relies upon hydrophobic interactions between the resins and sample molecules. In hydrophobic interaction chromatography (HIC), the interactions generally require high salt buffer concentrations to reduce the solvation of the molecules in solution, thereby revealing hydrophobic regions in the sample molecules that are consequently adsorbed by the hydrophobic resin. See U.S. Pat. No. 5,641,870. As with ion exchange chromatography, it is often difficult to achieve the correct balance of ionic strength and pH to afford useful separations of sample molecules as discussed, for example, by S. C. Burton et al. "Hydrophobic Charge Induction Chromatography: Salt Independent Protein Adsorption and Facile Elution With Aqueous Buffer," 814 *J. Chromatography A* 71-81 (1998). Many conventional HIC resins thus operate at neutral pH, but require high salt conditions, which pose practical difficulties as discussed below.

For these reasons, as noted above, the separation of proteins and other biomolecules from physiological isolates requires processing of the isolates to enforce the correct pH and ionic strength requirements of ion exchange and HIC resins. Conventional solutions to overcome the ionic strength problem in particular include diluting a sample with very low ionic strength buffers (or even water) and dialyzing the sample against a buffer with the desired ionic strength. Both of these operations, however, are time consuming and are often incompatible with large scale biomolecule separations.

More recent attempts to overcome the above-mentioned difficulties focus upon protein separation based on dual-mode ligands, which seek to incorporate, for example, ionic and hydrophobic features into the same capture ligand, and thereby lessen the need to employ high salt conditions for protein capture. See L. Guerrier et al. "New Method for the Selective Capture of Antibodies Under Physiological Conditions," 9 *Bioseparation* 211-221 (2000) for a discussion of resins that combine mild hydrophobic association and charge induction for protein capture. Other resins, by contrast to the present invention, rely upon thiophilic ligands that incorporate heterocyclic moieties, such as mercaptonicotinic acid as disclosed by G. H. Scholz et al. "Salt-Independent Binding of Antibodies from Human Serum to Thiophilic Heterocyclic Ligands," 709 *J. Chromatography B: Biomedical Sciences and Applications* 189-196 (1998).

In principle, powerful analytical methods can be realized with the ion exchange and HIC adsorbents discussed above. For example, the rapid identification of disease markers by analyte/adsorbent interactions would supplant the tedious and time consuming work required in conventional clinical diagnostics in order to prepare reagents that specifically bind to such markers. Additionally, the direct and rapid identification of differentially expressed proteins would be a significant benefit to the field, thereby circumventing, for example, the long process of polypeptide isolation and subsequent immunization to produce desired immunoglobulins. The above-mentioned shortcomings of conventional adsorbents limit the sensitivity and resolution of such analytical tools, however.

Accordingly, a continued need exists in the art for improved ion exchange chromatographic and HIC materials that exhibit high binding capacity and specificity, that can be regenerated extensively without suffering physiochemical degradation, and that can function under physiological pH and/or ionic strength. A need also exists for improved biochemical analytic tools that are useful for the rapid identification of biologically important molecules.

SUMMARY OF THE INVENTION

To address these and other needs, the present invention provides a chromatographic material comprising (a) a terminal binding functionality; (b) a hydrophobic linker comprising at least one functionality that is different from the terminal binding functionality; and (c) a solid support, wherein the hydrophobic linker links the terminal binding functionality to the solid support. Within these provisions, the chromatographic material is capable of binding bovine albumin at physiological ionic strength.

The chromatographic material of the invention preferably conforms to general formula (I):

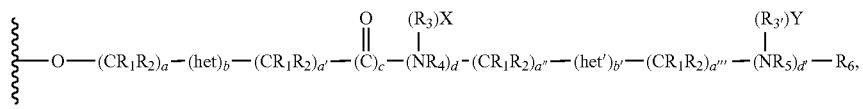

wherein $R_1$, $R_2$, $R_4$, and $R_5$, at each occurrence, are independently selected from the group consisting of H, $C_{1-6}$-alkyl, $C_{1-6}$-alkoxy, $C_{1-6}$-alkyl-$C_{1-6}$-alkoxy, aryl, $C_{1-6}$-alkaryl, —NR'C(O)R", —C(O)NR'R", and hydroxy. R' and R" are independently selected from $C_{1-6}$-alkyl, and no more than one of $R_1$, and $R_2$ is hydroxy. $R_6$ is selected from the group consisting of H, $C_{1-6}$-alkyl, aryl, $C_{1-6}$-alkaryl, —C(O)OH, —S(O)$_2$OH, and —P(O)(OH)$_2$. $R_3$ and $R_{3'}$, together with X and Y, respectively, may independently be absent or present, and if present, then $R_3$ and $R_{3'}$, are independently selected from the group consisting of H, $C_{1-6}$-alkyl, $C_{1-6}$-alkoxy, $C_{1-6}$-alkyl-$C_{1-6}$-alkoxy, aryl, and $C_{1-6}$-alkaryl. X and Y, independently of each other, represent anions. Het and het' are heteroatom moieties independently selected from the group consisting of —O—, —S—, —S(O)—, and —S(O)$_2$—. Subscripts a, a', a", and a''' are independently selected from the integers 0 through 6; b and b' are independently 0 or 1; c is 0 or 1, and if c is 1, then (R$_3$)X is absent; and d and d' are independently 0 or 1. In formula (I), the wavy line represents the solid support.

In certain embodiments, at least one or two of a, a', a", and a''' is 2, preferably where at least one of a, a', a", and a''' is also 3. In other embodiments, at least one or two of a, a', a", and a''' is 3.

Preferred chromatographic materials are those wherein a is 3, het is S, and b is 1. Within these constraints, a' is preferably 2, 3, 4, 5, or 6; b' is 0; c and d are both 0 or 1; and d' is 1. In other materials, d' can be 0 or 1. Preferably, $R_1$ and $R_2$ are independently selected from H and $C_{1-6}$-alkyl, more preferably each of $R_1$ and $R_2$ is H.

In one group of preferred terminal groups, $R_{3'}$, $R_5$, and $R_6$ are independently selected from the group consisting of H, $C_{1-6}$-alkyl, aryl, and $C_{1-6}$-alkaryl, preferably from $C_{1-6}$-alkyl and aryl, and most preferably from $C_{1-6}$-alkyl. Exemplary groups in this context are methyl and ethyl. In this embodiment it is preferred that one of a" and a''' 1 while the other is 1 or 2, and that (R$_{3'}$)Y is absent.

Another preferred subset of chromatographic materials are those wherein d' is 0 and $R_6$ is preferably H, $C_{1-6}$-alkyl, aryl, or $C_{1-6}$-alkaryl, more preferably, $C_{1-6}$-alkyl and aryl. $R_6$ is most preferably phenyl. Alternatively, $R_6$ is —C(O)OH, —S(O)$_2$OH, or —P(O)(OH)$_2$. In combinations, one of a" and a''' preferably is 1 and the other is 1 or 2.

In another embodiment, a is 3, a' is 2, a is 3; a' is 2; b is 1; and each $R_1$ and $R_2$ in (CR$_1$R$_2$)$_a$ and (CR$_1$R$_2$)$_{a'}$ is H, except that one of $R_2$ in (CR$_1$R$_2$)$_a$ is optionally OH. Preferably, one of $R_2$ in (CR$_1$R$_2$)$_a$ is OH. More preferably, each of a", a''', and b' is 0.

In another embodiment, a" is 3; a''' is 2; b' is 1; and each $R_1$ and $R_2$ in (CR$_1$R$_2$)$_{a''}$ and (CR$_1$R$_2$)$_{a'''}$ is H, except that one of $R_2$ in (CR$_1$R$_2$)$_{a''}$ is optionally OH. Preferably, one of $R_2$ in (CR$_1$R$_2$)$_{a''}$ is OH. More preferably, each of a, a', and b" is 0.

In still another embodiment, a is 3; a' is 3; b is 1; and each $R_1$ and $R_2$ in (CR$_1$R$_2$)$_a$ and (CR$_1$R$_2$)$_{a'}$ is H. Preferably, each of a", a''', and b' is 0.

In yet another embodiment, a" is 3; a''' is 3; b' is 1; and each $R_1$ and $R_2$ in (CR$_1$R$_2$)$_{a''}$ and (CR$_1$R$_2$)$_{a'''}$ is H. Preferably, each of a, a', and b is 0.

In another embodiment, a is 3; a' is 5; b is 1; and each $R_1$ and $R_2$ in (CR$_1$R$_2$)$_a$ and (CR$_1$R$_2$)$_{a'}$ is H.

In an additional embodiment, b' is 0; one of a" and a''' is 2 or 3, the other being 0; and each $R_1$ and $R_2$ in (CR$_1$R$_2$)$_{a''}$ and (CR$_1$R$_2$)$_{a'''}$ is H, except that one of $R_2$ in (CR$_1$R$_2$)$_{a''}$ and (CR$_1$R$_2$)$_{a'''}$ is optionally OH. Preferably, a" or a''' is 3 and one of $R_2$ in (CR$_1$R$_2$)$_{a''}$ and (CR$_1$R$_2$)$_{a'''}$ is OH.

In another embodiment, a or a' is 3, the other being 0; a" or a''' is 3; each of b, b', and c is 0; and d is 1. Preferably, d' is also 1.

In still another embodiment, each of $R_1$ and $R_2$ are H; $R_3$, $R_{3'}$, $R_4$, $R_5$, and $R_6$ are independently selected from the group consisting of H, $C_{1-6}$-alkyl, aryl, and $C_{1-6}$-alkaryl; het is S; a is 3; a' is selected from the group consisting of 2, 3, 4, 5, and 6; one of a" and a''' is 1 and the other is 1 or 2; and b is 1 and b' is 0.

The most preferred chromatographic materials are represented by the following formulae:

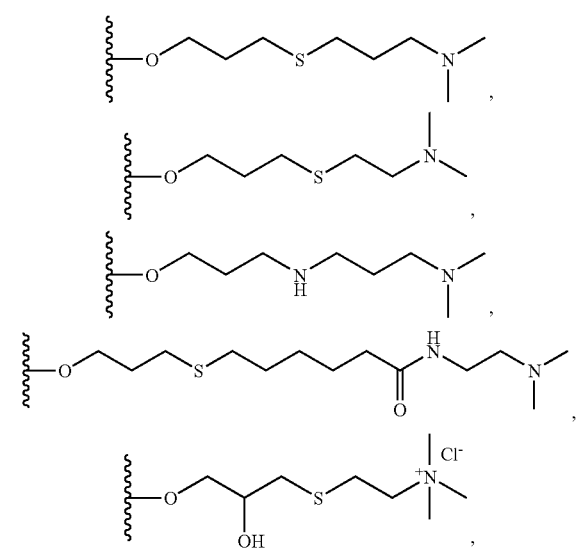

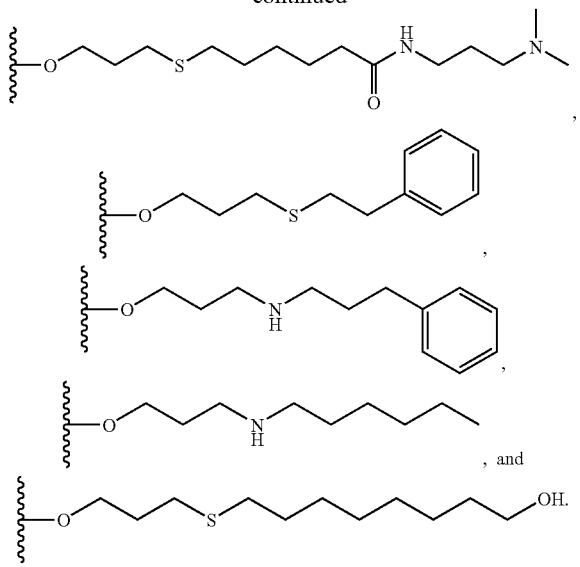
,

In certain embodiments, the solid support is an organic material. Preferably, the organic material is one selected from the group consisting of cellulose, agarose, dextran, polyacrylates, polystyrene, polyacrylamide, polymethacrylamide, copolymers of styrene and divinylbenzene, and mixtures thereof.

In other embodiments, the solid support an inorganic material. Preferably, the inorganic material is one selected from the group consisting of silica, zirconia, alumina, titania, ceramics, and mixtures thereof.

The solid support can be in the form of a bead or particle. Alternatively, the solid support is planar. In the latter case, the chromatographic material can be in the form of a biochip. Preferred solid supports in this context include a metal, metal oxide, silicon, glass, a polymer, and a composite material. Biochips are particularly preferred wherein a multitude of terminal binding functionalities and the hydrophobic linkers to which the terminal binding functionalities are linked are segregated into a plurality of addressable locations on the solid support. In this scenario, at least two different addressable locations comprise the same terminal binding functionality and hydrophobic linker. The biochip can be a mass spectrometer probe.

The invention also provides a chromatography column, comprising (a) a tubular member having an inlet end and an outlet end; (b) first and second porous members disposed within said tubular member; and (c) a chromatographic material according to this invention packed within the tubular member between the first and second porous members. In some embodiments, the chromatography column volume is between about 1 microliter and about 5000 liters. Preferably, the column volume is between about 1 liter and about 100 liters. The column may comprise one or more fluid control devices for flowing a liquid sample upward or downward through the chromatographic material.

The invention also provides for a method for the separation of at least one substance from a sample. The method entails (a) contacting a chromatographic material according to this invention with a liquid sample that comprises at least one substance, whereby the substance adsorbs to the chromatographic material; (b) adjusting the pH, ionic strength, or both such that the substance desorbs from the resin. Preferably, the method further comprises washing the chromatographic material obtained in (a) with an equilibrium buffer.

In the most preferred embodiments, the substance to be separated is a biological substance. The biological substance is preferably selected from of proteins, viruses, nucleic acids, carbohydrates, oligosaccharides, polysaccharides, lipids, and lipopolysaccharides. More preferably, the biological substance is a protein, such as an immunoglobulin, hormone, clotting factor, cytokine, peptide, polypeptide, or enzyme. The most preferred substance is an immunoglobulin.

In one aspect of the method, the liquid sample is at physiological ionic strength. The liquid sample may also be at physiological pH. Preferred ionic strengths in this regard are between about 0.1 M and about 0.2 M. Additionally, the concentration of the biological substance can be the physiological concentration.

In some embodiments, the method further comprises adjusting the ionic strength of the liquid sample to physiological ionic strength prior to step (a). In other embodiments, the method entails only increasing the ionic strength.

The method may be accomplished via several modes. These include fixed bed, fluidized bed, or batch chromatography.

The invention also contemplates a method of detecting an analyte, comprising (a) contacting an addressable location of the present chromatographic material with a sample comprising the analyte. This fixes the analyte to the chromatographic material. The analyte is detected by virtue of its binding to the terminal binding functionality and hydrophobic linker, preferably in a mass spectrometer. In the latter scenario, the addressable location is positioned proximately to a laser beam in the mass spectrometer, preferably where the detecting comprises irradiating the chromatographic material at the addressable location with a laser pulse for a time and power sufficient to desorb and ionize the analyte. The mass spectrometer can be a gas phase ion spectrometer.

In some embodiments of the method, the sample is a blood sample. Preferably, the blood sample is a serum sample.

The invention also contemplates a process for making the chromatographic material of this invention. The method generally comprises activating the solid support by contacting the solid support with one functionality of a bifunctional reagent that comprises part or all of the hydrophobic linker to bind the reagent to the solid support. The activated solid support is then reacted with a reagent that comprises the terminal binding functionality to form a bond between the hydrophobic linker and the terminal binding functionality. The bifunctional reagent may comprise at least two functional groups including but not limited to chloro, bromo, iodo, epoxide, carboxyl, ester, aldehyde, ketone, amido, alkenyl, cyano, and imino.

In one embodiment, the contacting step provides discreet spots of activated solid support. In this context, the chromatographic material preferably is in the form of a biochip.

DETAILED DESCRIPTION OF THE PREFERRED EMBODIMENTS

The present invention provides a chromatographic material that is an effective adsorbent for use in separating and isolating a variety of substances, including biologically relevant molecules. The chromatographic material of this invention may be used, for example, in preparative techniques, such as column chromatography, and in analytical devices, such as biochips.

One advantage of the present chromatographic material described herein is its high selectivity and specificity for biological substances such as proteins, together with the avoidance of costly and often detrimental cleaning processes required for prior art substrates. A second advantage is that the chromatographic material of the invention is ideally suited for use with biological samples at physiological ionic strength pH and/or physiological pH, thereby obviating the need for ionic strength and/or pH adjustments and the addition of lyotropic salts for desorption as prescribed by conventional materials. A third advantage is the high biological molecule binding capacity of the present substrates, which, in view the low cost of reagents employed to prepare them, presents significant economic gains over the use of specialized prior art chromatographic materials. Consequently, it is possible to manipulate smaller volumes of a sample, to reduce processing time, or to process a large amount of a sample per unit column volume.

I. Chromatographic Material

The chromatographic material of this invention comprises a solid support and a terminal binding functionality that is attached to the solid support via a hydrophobic linker. The terminal binding functionality serves to attract in part a substance in a sample. The hydrophobic linker comprises at least one functionality that is different from the terminal binding functionality, and typically contains a sulfur and/or a nitrogen atom. Overall, therefore, the linker presents a hydrophobic, and possibly thiophilic, region between the solid support and terminal binding functionality. The functionalities can give rise to a range of intermolecular forces; thus, the chromatographic material provides complementary modes of selectively attracting substances.

A. Functionalities

The terminal binding functionality may be selected according to the properties of the substance that is desired to be separated and according to the complementary characteristics of the hydrophobic linker. For example, where the terminal binding functionality is an anion or cation exchange group, it is desirable to maintain ancillary modes of sample interaction by tailoring the linker to be at least hydrophobic. In this embodiment, the hydrophobic linker can contain an anion or cation exchange group, but in accordance with the provisions of the invention, the linker preferably contains at least one functionality that is different from the anion or cation exchange group, respectively. A preferred functionality in this regard is a sulfur-containing group, such as —S— or —S(O)$_2$—.

In other embodiments, the terminal binding functionality itself is a hydrophobic group. Thus, although the linker generally is composed of hydrophobic regions, the linker must contain at least one functionality that is not the same as the hydrophobic terminal binding functionality. Functionalities in this regard include, of course, anion and cation exchange groups, possibly together with the sulfur-containing moieties mentioned above.

The "terminal binding functionality," as contemplated herein, resides by definition at the end of the hydrophobic linker, and therefore is believed to exert the greatest contribution to the adsorbent properties of the inventive chromatographic material. In some embodiments, the terminal binding functionality is an anion exchange group, such as amines and quaternary ammonium salts. In other embodiments, the terminal binding functionality is a cation exchange group. In yet other embodiments, hydrophobic groups, as defined below, are most suitable for the terminal binding functionality.

The requirements for the hydrophobic linker include the presence of at least one functionality that is different from the terminal binding functionality. It is believed that this functionality, by virtue of it being embedded within the hydrophobic linker, confers secondary adsorbent properties to the inventive chromatographic material.

The term "hydrophobic," as used herein, generally refers to a non-polar chemical moiety that is understood in the art to repel polar entities such as water, or equally, to attract other hydrophobic entities such as hydrophobic regions in proteins. Exemplary hydrophobic groups contemplated for this invention include but are not limited to alkyl, aryl, and alkaryl groups. Typical hydrophobic groups are simple hydrocarbon chains such as ethyl and propyl, or when embedded into another group, ethylene or propylene spacers, respectively. While no general standard exists for evaluating hydrophobicity, it is understood within the context of this invention that at least a 2-carbon chain is sufficient to create a hydrophobic region. The overall hydrophobic character of a group, however, is not negated by the presence of a limited number of polar groups, but it is recognized in the art that the presence of ionic or polar groups generally require longer or large hydrophobic groups to maintain the overall hydrophobic character. See U.S. Pat. No. 3,917,527. Thus, for example, the hydrophobic linker of this invention may be substituted with an amine or quaternary ammonium group, an ether or thioether, an amide, or a hydroxyl group.

Preferred embodiments of the invention conform to the general formula (I):

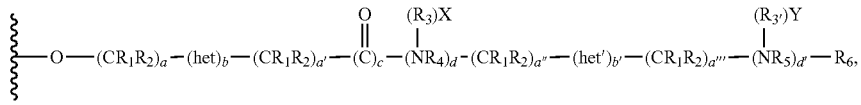

separated and according to the complementary characteristics of the hydrophobic linker. For example, where the terminal binding functionality is an anion or cation exchange group, it is desirable to maintain ancillary modes of sample interaction by tailoring the linker to be at least hydrophobic. In this formula, $R_1$, $R_2$, $R_4$, and $R_5$ are independently selected from H, $C_{1-6}$-alkyl, $C_{1-6}$-alkoxy, $C_{1-6}$-alkyl-$C_{1-6}$-alkoxy, aryl, $C_{1-6}$-alkaryl, —NR'C(O)R'', —C(O)NR'R'', and hydroxy. Preferably, $R_1$, $R_2$, $R_4$, and $R_5$ are independently selected from H and $C_{1-6}$-alkyl. The most preferred embodiments are those in which $R_1$ and $R_2$ are H, while $R_4$ and $R_5$ are $C_{1-6}$-alkyl.

Depending upon the desired terminal binding functionality, $R_6$ is selected from the group consisting of H, $C_{1-6}$-alkyl, aryl, $C_{1-6}$-alkaryl, —C(O)OH, —S(O)$_2$OH, and —P(O)(OH)$_2$. The terminal binding functionality as a whole is thus represented generally by —(NR$_5$)(R$_{3'}$)Y—R$_6$ in formula (I). In one preferred embodiment, for example, d' is 1, thus giving the terminal binding functionality as an amine (when (R$_{3'}$)Y is absent) or a quaternary ammonium salt (when (R$_{3'}$)Y is present). In these embodiments, $R_6$ is preferably $C_{1-6}$-alkyl.

In other embodiments, d' is 0, thus providing for a terminal binding functionality that is represented predominantly by $R_6$. In these cases, $R_6$ is preferably chosen from H, $C_{1-6}$-alkyl, aryl, and $C_{1-6}$-alkaryl groups when a hydrophobic terminal binding functionality is desired. Where the terminal binding functionality is a cation exchange group, $R_6$ is accordingly chosen from —C(O)OH, —S(O)$_2$OH, and —P(O)(OH)$_2$.

The moieties (R$_3$)X and (R$_{3'}$)Y, when they are present in formula (I), form quaternary ammonium salts with the respective nitrogen atoms to which each moiety is bound. As required by formula (I), X and Y represent anions. No particular requirements restrict the identity of these anions, so long as they are compatible with the prescribed use of the chromatographic material. Exemplary anions in this regard include fluoride, chloride, bromide, iodide, acetate, nitrate, hydroxide, sulfate, carbonate, borate, and formate.

The balance of formula (I), therefore, generally represents the hydrophobic linker. Consistent with the definition of a hydrophobic group as defined hereinabove, the linker is hydrophobic overall, which property is achieved preferably by incorporating alkylene chains into the linker, corresponding to the selection of a, a', a'', and a'''. Preferably, at least one of a, a', a'', and a''' is 2 or 3, more preferably at least two of a, a', a'', and a''' are 2 or 3, and most preferably a is 3 while a' is 2, 3, 4, 5, or 6.

In preferred embodiments, the linker is thiophilic in addition to being hydrophobic. Accordingly, one or both of het and het' in formula (I) are chosen from increasingly thiophilic groups —S—, —S(O)—, and —S(O)$_2$—, S being most preferred. In the most preferred chromatographic material, het is S while het' is absent.

The inventors have discovered that certain subsets of chromatographic materials are particularly efficacious. This is so because the materials present significant patches or regions of hydrophobicity in the hydrophobic linker, which property is generally achieved by coupling alkylene fragments together. Thus, at least two of $(CR_1R_2)_a$, $(CR_1R_2)_{a'}$, $(CR_1R_2)_{a''}$ and $(CR_1R_2)_{a'''}$ represent two unsubstituted ethylene groups (i.e., —CH$_2$—CH$_2$—). Alternatively, the hydrophobic linker can comprise at least two unsubstituted propylene groups. That is, at least two of $(CR_1R_2)_a$, $(CR_1R_2)_{a'}$, $(CR_1R_2)_{a''}$ and $(CR_1R_2)_{a'''}$ represent two propylene groups (i.e. —CH$_2$—CH$_2$—CH$_2$—). In another embodiment, the hydrophobic linker can comprise at least one unsubstituted ethylene group and at least one mono-substituted propylene group. For example, at least one of $(CR_1R_2)_a$, $(CR_1R_2)_{a'}$, $(CR_1R_2)_{a''}$ and $(CR_1R_2)_{a'''}$ is —CH$_2$—CH$_2$— and at least one is —C$_3$H$_5$(OH)—. In another embodiment, the hydrophobic linker can comprise at least two mono-substituted propylene groups. For example, at least two of $(CR_1R_2)_a$, $(CR_1R_2)_{a'}$, $(CR_1R_2)_{a''}$ and $(CR_1R_2)_{a'''}$ are —C$_3$H$_5$(OH). In these embodiments the alkylene groups can be separated by a heteroatom or a group comprising a heteroatom, such as —O—, —S—, —NH— or —C(O)N(H)—. All combinations of these are contemplated.

More specifically, one embodiment incorporates an unsubstituted propylene group and an unsubstituted ethylene group that are separated by het or het' in general formula (I), in which, for example, a (or a'') is 3, a' (or a''' is 2), and b (or b') is 1. In this embodiment, it is possible, however, to substitute the propylene group with one hydroxyl group and maintain the overall hydrophobicity of the linker.

In another preferred embodiment, the hydrophobic linker comprises two unsubstituted propylene groups that are separated by het or het'. Thus referring to general formula (I), a and a' are both 3 while b is 1, or a'' and a''' are both 3 while b' is 1.

In yet another preferred embodiment, the hydrophobic linker comprises an unsubstituted propylene group and at least an unsubstituted pentylene group that are separated by het, thus corresponding to a being 3, a' being 5, and b being 1 in general formula (I). In this embodiment, the propylene group can be substituted once with a hydroxyl group.

In still another preferred embodiment, the hydrophobic linker comprises two unsubstituted propylene groups that are separated by one amino moiety. Referring therefore to general formula (I), a or a' is 3, the other being 0; a'' or a''' is 3; het and het' are absent; and c is 0 while d is 1.

In general formula (I), the wavy line represents the solid support to which the hydrophobic linker is attached. It is understood for the purpose of clarity, however, that general formula (I) depicts only one (1) linker-terminal binding functionality as being tethered to the solid support. The inventive chromatographic materials actually exhibit linker-terminal binding functionality densities of about 50 to about 150 μmol/mL chromatographic material, preferably about 80 to about 150 μmol/mL, and more preferably 100 to about 150 μmol/mL.

"Alkyl", as used herein, refers to a straight or branched hydrocarbon having 1 to 12 carbon atoms, preferably 1 to 6 carbon atoms. Exemplary alkyl groups are methyl, ethyl, propyl, butyl, pentyl, and hexyl. An alkyl fragment that is part of a chain is necessarily divalent and is referred to as an "alkylene" group.

"Aryl," as used herein, refers to a cyclic, fused or non-fused, fully aromatic hydrocarbon that has 6 to 12 carbon atoms. Exemplary aryl groups include but are not limited to phenyl, naphthyl, and biphenyl.

"Alkaryl" thus refers to an alkyl group that is substituted by an aryl group, as each are defined above. Exemplary alkaryl groups include but are not limited to benzyl and phenethyl.

"Alkoxy," as used herein, refers to a group of the formula —O-alkyl, wherein alkyl is defined above. Exemplary alkoxy groups include but are not limited to methoxy and ethoxy.

"Alkylalkoxy," as used herein, is an alkyl moiety that is substituted by an alkoxy moiety, i.e., corresponding to the general formula -alkylene-O-alkyl.

As mentioned above, a key advantage of the present invention is that the chromatographic material binds a variety of biological substances at physiological ionic strength. Accordingly, it is understood that the invention preferably does not include chromatographic sorbents that do not bind bovine albumin at physiological ionic strength.

Without limiting themselves to any particular theory, the inventors believe that the chromatographic material of this invention operates via combined interactions between the chromatographic material and a substance. In the context of separating biological substances, it is believed that mild hydrophobic and/or thiophilic interactions between the chromatographic material and a biological substance reinforce the stronger electrostatic attractions arising from anion or cation exchange terminal groups. It is also believed that mild ionic and thiophilic interactions between the chromatographic material and a biological substance reinforce the strength of interactions arising from hydrophobic terminal groups. The primary advantage that flows from these combined interactions is that salts at physiological ionic strength do not disrupt the selective adsorbent properties of the chromatographic material.

B. Solid Support

This invention contemplates a solid support to which the hydrophobic linker and terminal binding functionality are attached. Two different formats are contemplated in particular. In one format, the solid support is of the form typically used for chromatography media, that is, a bead or particle. These beads or particles are derivatized with the combination hydrophobic linker and terminal binding functionality. The beads or particles form a chromatography medium that one can use to pack a column, for example. In another format, the solid support takes the form of a chip, that is, a solid support having a generally planar surface to which the hydrophobic linker and terminal binding functionality can be attached, covalently or otherwise. Chips that are adapted to engage a probe interface of a detection device such as a mass spectrometer are also called "probes."

1. Beads and Particles

In accordance with the teachings of this invention, the chromatographic material first comprises a solid support, which may comprise an organic material. Exemplary organic materials are polysaccharides, such as cellulose, starch, agar, agarose, and dextran. Hydrophilic synthetic polymers are contemplated, including substituted or unsubstituted polyacrylamides, polymethacrylamides, polyacrylates, polymethacrylates, polyvinyl hydrophilic polymers such as polyvinyl alcohol, polystyrene, polysulfone, and copolymers or styrene and divinylbenzene, and mixtures thereof. Alternatively, inorganic materials may be used as the solid support material. Such inorganic materials include but are not limited to porous mineral materials, such as silica; hydrogel-containing silica, zirconia, titania, alumina; and other ceramic materials. It is also possible to use mixtures of these materials, or composite materials formed by copolymerization of or by an interpenetrated network of two materials, such as those disclosed in U.S. Pat. Nos. 5,268,097, 5,234,991, and 5,075,371.

The solid support may be in the form of beads or irregular particles of about 0.1 mm to about 1000 mm in diameter. Alternatively, the solid support can be fashioned into fibers, membranes, or sponge-like materials permeated with holes in the micron to multi-millimeter sizes.

2. Biochip

A preferred embodiment has the chromatographic material, thus described, in a "biochip" or microarray format, where the material presents a generally planar surface to which is attached a capture reagent: in the present context, a combination of a hydrophobic linker and a terminal binding functionality. Thus, a biochip presents a defined region or site—more typically, a collection of defined regions or sites—on which analytes may be captured selectively. Upon capture, analytes can be detected and, optionally, characterized by a variety of techniques, described in more detail below.

Thus, the solid support can comprise a metal, such as gold, aluminum, iron, titanium, chromium, platinum, copper and their respective alloys. Such metals can be derivatized on their surfaces with silicon dioxide, for instance, to provide reactive groups for linking. One method of derivatizing a metal surface is to sputter a metal oxide, such as silicon oxide, onto the metal surface. Alternatively, the solid support can comprise silicon, glass or an organic polymer, such as a plastic. In certain embodiments, the solid support can be transparent.

Notably, the arrangement of sites on the surface of a biochip of the invention preferably permits interrogation of multiple sites at the same time, to achieve higher throughput and speed. The use of a biochip is therefore essentially equivalent to concurrently conducting multiple chromatographic experiments, each with a different chromatographic column, but the present biochip has the advantage of requiring only a single system.

Thus, it is preferable that an inventive biochip comprise a plurality of addressable locations, and to each such location is tethered a unique combination of hydrophobic linker and terminal binding functionality. The biochip can incorporate a single addressable location or as many as 8, 10, 16, 100, 1000, 10,000 or more addressable locations, which need only be as large as an impinging energy source, such as a laser. In this regard, "addressable" connotes a position on the chromatographic material that can be located, e.g., by an energy source, using an appropriate addressing scheme or algorithm. Thus, each addressable location or subsets of locations can bind a biological substance preferentially, and the binding can be located by virtue of the fact that capture occurs at a defined location on the biochip.

The addressable locations can be arranged in any pattern but preferably appear in regular patterns, such as lines or orthogonal arrays, or even as curves, such as circles. Circular arrangements of the addressable locations are particularly useful on disk-shaped biochips. Thus arranged, the addressable locations can provide known gradients of binding capacity on the chromatographic material.

In a particularly preferred embodiment, the present chromatographic material in the form of a biochip is a probe for use in a detection instrument, such as a mass spectrometer, therewith providing a powerful analytic tool for the capture and identification of known and unknown biological analytes. Illustrative probes are described in U.S. Pat. No. 6,225,047, which is incorporated herein by reference. For example, a mass spectrometer probe ("MS probe") refers to a device that, when positionally engaged in an interrogatable relationship to an ionization source, e.g., a laser desorption/ionization source, and in concurrent communication at atmospheric or subatmospheric pressure with the detector of the preferred Laser Desorption/Ionization Time-Of-Flight spectrometer, can be used to introduce ions derived from an analyte into the spectrometer. Preferred laser sources include nitrogen lasers, Nd-Yag lasers and other pulsed laser sources. Thus, a MS probe typically is reversibly engageable (e.g., removably insertable) with a probe interface that positions the MS probe in an interrogatable relationship with the ionization source and in communication with the detector.

In another embodiment, the biochip comprising an attached hydrophobic linker and terminal binding functionality is adapted for SEND (Surface Enhanced Neat Desorption). This is accomplished by attaching to the solid support molecules that absorb laser energy and promote desorption and ionization of an analyte into the gas phase. The energy absorbing molecules are attached to the surface in such a manner that they do not envelop the analyte in a matrix crystal and they are not desorbed upon contact with ionizing energy. SEND is further described in U.S. Pat. No. 6,124,137 (Hutchens and Yip) and WO 03/064594 (Kitagawa).

II. Process for Making the Chromatographic Material

The terminal binding functionality described above is chemically immobilized on the solid support by forming covalent bonds between the solid support and the hydrophobic linker, and between the hydrophobic linker and terminal binding functionality. In typical scenarios, the solid support is first treated with a bifunctional reagent which serves to introduce onto the solid support reactive groups that form part or all of the hydrophobic linker. For some solid supports, such as cellulose, composites containing a hydrogel, or other materials presenting hydroxyl groups, it is often advantageous to deprotonate the hydroxyl groups with a hydroxide source, for example, prior to reaction with a bifunctional reagent. The bifunctional reagent is capable of reacting both with the solid support and with reagents that contain the terminal binding functionality. Illustrative bifunctional reagents, which contain the same or different functional groups, include but are not limited to epichlorhydrin, epibromhydrin, dibromo- and dichloropropanol, dibromobutane, ethylene glycol diglycidylether, butanediol diglycidylether, divinyl sulfone, allylglycidylether, and allyl bromide. Allyl heterofunctional compounds, such as allyl bromide, are preferred bifunctional reagents.

Once functionalized, the solid support is then washed extensively with one or more solvents to remove unreacted bifunctional reagent, reaction byproducts, or both. A typical solvent used in this regard is water.

The terminal binding functionalities then are introduced by way of reagents that contain such functionalities. Such reagents react with the functional groups that are presented by the functionalized solid support as described above.

The particular pairing of a bifunctional reagent with a terminal binding functionality reagent is guided by well-known chemistries. For example, solid supports that are functionalized with epoxides may undergo reactions with mercapto, hydroxy, or amino-containing reagents to furnish a substrate with ethylene-containing linking groups. Other solid supports that are modified with allyl bromide, for example, present alkene groups that can be reacted directly with mercapto-containing reagents, thereby providing hydrophobic linkers that contain sulfur atoms. Alternatively, the alkene groups can be further brominated to furnish suitably reactive bromo derivatives.

Preferred embodiments include those in which the hydrophobic linker comprises sulfur atoms to increase the thiophilicity of the resultant chromatographic material. Sulfur atoms can be introduced in several ways, depending upon the source of the sulfur atom. The first, as described above, is the direct reaction of the solid support with a sulfur-containing bifunctional reagent such as divinylsulfone (DVS). In this instance, the reagent comprising the terminal binding functionality need only to react with the vinyl group presented by the DVS-activated solid support.

An alternative way to introduce sulfur atoms into the hydrophobic linker is by way of the reagents that comprise the terminal binding functionalities. In preferred embodiments, suitable reagents in this regard already possess sulfur atoms in their structures, e.g., trimethylaminoethylmercaptan, trimethylaminopropylmercaptan, and diethylaminoethylmercaptan. Other reagents that do not contain sulfur but contain a primary amine, such as diethylaminopropylamine, dimethylaminopropylamine, and their corresponding quaternary ammonium salt derivatives, can be reacted first with N-acetyl-homocysteine thiolactone. In this scenario, the products are thiol-containing reagents that contain part of the hydrophobic linkers and comprise the terminal binding functionalities. The thiol portions of these reagents thus react according to known methods with suitably activated solid supports, such as those presenting alkene and bromo groups as described above.

In a second alternative route, the solid support, activated as described above, is treated with an intermediate bifunctional reagent containing the desired sulfur-containing moiety. The product of this reaction is then treated with the reagent comprising the terminal binding functionality. An illustrative example in this regard is the reaction between an allyl-activated solid support, as described above, with mercaptohexanoic acid. The resultant pendant carboxyl groups can be reacted with any convenient terminal binding functionality reagent that bears, for example, a primary amine. In embodiments that employ this methodology, it may be necessary to use coupling reagents such as N-ethoxycarbonyl-2-ethoxy-1,2-dihydroquinoline (EEDQ) or commonly-known carbodiimides such as dicyclohexylcarbodiimide (DCC).

concentration of immobilized hydrophobic linker and terminal binding functionality can vary between a fraction of a micromole to several hundred micromoles per milliliter of solid support, depending upon the concentration of bifunctional reagent used to make the solid support. Low concentrations of the immobilized group typically result in low separation capacity of the chromatographic material, whereas high concentrations generally lead to increased capacity.

III. Methods of Using the Chromatographic Material

A benefit of the present invention is the ability of the inventive chromatographic material to bind analytes at physiological ionic strength, in contrast to conventional chromatographic materials that require the use of extreme ionic strengths. Thus in preferred embodiments, the chromatographic material of the present invention can be used to separate and isolate a variety of substances, including biologically relevant molecules such as proteins, viruses, nucleic acids, carbohydrates, and lipids. In many instances, the substances can be separated without any modification to raw feedstock under the conditions prescribed for the use of the chromatographic material as described below. Other substances that are suitable for separation include oligo- and polysaccharides, pigments, lipopolysaccharides, polypeptides, and synthetic soluble polymers. The biological substances typically derive from, or are contained in, sources including but not limited to liquid samples such as saliva, blood, urine, lymphatic fluid, prostatic fluid, seminal fluid, milk, milk whey, organ extracts, plant extracts, cell extract, cell culture media, fermentation broths, serum, ascites fluid, and transgenic plant and animal extracts.

In this context, a particularly preferred class of biological substances is immunoglobulins. The "immunoglobulins" category embraces whole immunoglobulins, including monoclonal and polyclonal antibodies, as well as Fab, $F(ab')_2$, $F_c$ and $F_v$ fragments thereof.

A. Method of Separating Substances

The liquid sample containing one or more biological substances is contacted with the chromatographic material of this invention for a period of time sufficient to allow at least one biological substance to bind to the chromatographic material. Typically, the contact period is between about 30 seconds to about 12 hours.

As mentioned above, an advantage of the present invention is that the pH, ionic strength, or both of the liquid sample need not be adjusted prior to contacting the sample with the chromatographic material. Additionally, it is not necessary to concentrate, dilute, or mix the sample with additives such as salts. Thus, it is possible to directly load a liquid sample onto the chromatographic material of this invention. The pH of liquid samples can be adjusted, however, to experimentally determined values that are optimized for adsorption. Typical capture pH values for a range of proteins is from about 4 to about 10. Preferably, a pH in the range of about 4 to about 7 promotes protein adsorption to those chromatographic materials that feature a cation exchange moiety, while a pH in the range of about 6 to about 10 will accomplish the same where anion exchange moieties are employed.

Many biological substances will readily adsorb to the chromatographic material at physiological ionic strength. Physiological ionic strength, as used herein, generally ranges from about 15 to about 20 mS/cm. Typical salt concentrations that correspond to this range fall within about 0.1 to about 0.2 M, preferably 0.14 to about 0.17 M.

The temperature at which the liquid sample is contacted with the chromatographic material varies between samples and a given chromatographic material. Preferably, the temperature is ambient, but can be changed.

After the sample is contacted with the chromatographic material, the chromatographic material is preferably washed with an equilibration buffer. As defined herein, an equilibration buffer is a buffer that is preferably of the pH at which the liquid sample was contacted with the chromatographic material. Furthermore, the equilibration buffer washes from the chromatographic material any substance that does not adsorb to the substrate. Suitable equilibration buffers include acetate buffer and phosphate buffered saline. The washing may be accomplished by bathing, soaking, or dipping the chromatographic material with bound biological substance into the equilibration buffer. Alternatively, the equilibration buffer may be rinsed, sprayed, or washed over the chromatographic material.

The desired biological substance typically is one that adsorbs to the chromatographic material. However, the invention contemplates scenarios in which the biological substance of interest is removed in the equilibration buffer washing. In this case, the substance may be isolated from the buffer by routine methods.

Biological substances that are adsorbed to the chromatographic material are then desorbed in one embodiment by adjusting the pH to a value where the substance can desorb. The pH at which desorption occurs will depend upon the substance and upon a given chromatographic material. For example, for chromatographic materials that comprise an anion exchange moiety, desorption generally occurs over a pH gradient starting at about pH 8 and decreasing to about pH 3. For chromatographic materials that comprise a cation exchange moiety, the pH gradient applied starts at about pH 4 and is increased to about pH 11. For chromatographic materials that feature primarily hydrophobic groups, the pH gradient for desorption starts at about pH 7 is decreased to about pH 3. In the last scenario, preferably an ionic strength gradient is also applied as described below. The pH can be adjusted by any routinely available reagent, such as aqueous solutions of Tris-HCl or carbonate buffers.

In some instances, as mentioned above, adjustment of the eluant ionic strength can increase effectiveness of the chromatographic material. Thus for chromatographic materials that comprise primarily hydrophobic groups, the ionic strength can be decreased concomitantly with pH. This is especially so for materials that additionally comprise —NH— moieties, which can give rise to mild ionic charges that become more effective as the ionic strength is decreased. The use of salt gradients is well-known in the art. Typically, salt concentrations for the present chromatographic material need not exceed about 0.5 M.

The desorbed biological substance is then collected. Typical purities of biological substances, such as antibodies, that are purified by the method of this invention range from about 70% to about 99%, preferably 85% to about 99%, and most preferably about 90% to about 99%.

The separation method described above can be adapted for use in a variety of techniques, including preparative methods employing fixed bed, fluidized bed, and batch chromatographies. Alternatively, the method can be practiced in the context of high throughput separation techniques that utilize small devices such as spin columns or multiwell plate formats where device volumes can be as small as a few microliters.

The techniques mentioned above comprise contacting a solution containing the biological substances with the chromatographic material, thereby leading to the selective adsorption of at least one biological substance in the solution by the chromatographic material. In the event of the desired biological substance(s) being fixed to the chromatographic material, the elution of the latter allows it or them to be separated and collected in a purified and concentrated form. If the desired biological substance remains in the treated solution (the other biological substances being fixed to the chromatographic material) then the desired separation is obtained directly by collecting the eluant.

When using batch adsorption/separation, the chromatographic material is added directly to the solution of biological substances, and the chromatographic material/biological substance mixture is gently agitated for a time sufficient to allow the biological substances to bind to the chromatographic material. The chromatographic material, with adsorbed biological substances, may then be removed by centrifugation or filtration, and the biological substances subsequently eluted from the chromatographic material in a separate step.

Alternatively, column chromatography may be used. In fixed bed column chromatography, the chromatographic material is packed into a column, and the solution which contains the biological substances to be separated is applied to the chromatographic material by pouring it through the chromatographic material at a rate that allows the biological substances to bind to the chromatographic material.

Advantages of fixed bed chromatography include minimal column volume and water consumption. The disadvantage of the column chromatography method is that the flow rate of liquids through the column is slow, and, therefore, time-consuming. This flow rate can be reduced even further if the material being applied to the column includes particulates, since such particulate material can "clog" the chromatographic material to some degree.

In fluidized bed column chromatography, a rising filtration flow and large/dense particles are used in order to maintain an equilibrium against the rising forces. An essentially vertical column composed of between 1 and 5 stages placed on top of the other is used, and the solution successively passes through each stage and is drawn off by an overflow on the upper part of the upper stage. Preferably, the column has three stages. Each stage, with the exception of the uppermost one, is separated by two distribution systems, one distributing the solution at the base of the stage in question, the other distributing the solution towards the stage located immediately above.

The advantages of a fluidized bed are higher flow rates at lower pressures as compared to fixed bed chromatography. Although the higher flow rates offer certain advantages to the chromatographic separation, the method has several shortcomings. The method requires either large particle diameter and/or high density chromatographic materials that expand only under high upward liquid velocity. Large diameter resins have less surface area per unit volume than small chromatographic materials used, and correspondingly have less surface binding capacity. This is why small bead chromatographic materials are preferred, in which case the bead chromatographic materials must be highly dense.

On the other hand, fluidized bed chromatography avoids many of the serious disadvantages of fixed beds, which include clogging, need for cleaning, compression and cleaning-induced chromatographic material deterioration. In fact, the fluidized bed allows free passage of solid impurities in the solution with no risk of clogging; less stringent cleaning is necessary so the life-span of the chromatographic materials is greatly increased. However, the chromatographic material for biological substances typically are not suitable for fluidized bed chromatography, having a density too close to that of water or being too small in granulometry. This makes it impossible to fluidize without drawing particles into the flux. Another problem with fluidized bed chromatography of biological substances relates to the large space between beads, which would result in a decrease in efficiency.

In view of these factors, batch and fixed bed chromatography have been the methods of choice in prior art separation techniques for biological substances. The present chromatographic material, on the other hand, can be used in batch, fixed bed, or fluidized bed chromatography.

B. Chromatography Column

Thus, in a preferred embodiment, the present invention provides a chromatography column, which is a tubular member packed with the chromatographic material described herein. The tubular member can be made of any suitable material, such as glass, plastic, or metal. The packed chromatographic material is abutted on each end by porous members that keep the substrate fixed within the tubular member.

In some embodiments, gravity flow of an eluant through a column is sufficient. In other embodiments, the column may comprise one or more fluid moving devices to achieve an upward flow of eluant through the column. Such devices include pumps, injectors, and any other device typically employed in association with chromatography equipment.

The chromatography column of this invention can be of any volume. For example, separations on a laboratory scale may warrant a column volume as small as about 1 milliliter or even about 1 microliter. Large scale purification and isolation of biological substances can be performed on columns as large as 5000 liters. More typical volumes are between 1 liter and 100 liters. The column is tubular in general shape, but is not otherwise particularly limited in length or diameter. Depending upon the context in which the column is employed, the column diameter can vary between about 0.5 mm to about 1000 mm. Additionally, the column length can vary between about 50 mm to about 1000 mm. Thus, the invention contemplates columns of a variety of dimensions and corresponding volumes.

The column of this invention can be used in tandem with columns comprising other chromatographic materials, which would be effective in eliminating different impurities from a sample. Thus, the advantages of the present column can be viewed as being complementary to the characteristics of other or conventional columns. In this context, such a tandem arrangement of columns would conserve eluants and equilibration buffer, thereby eliminating the need for additional sample manipulation and preparation.

C. Method of Detecting an Analyte

This invention provides a convenient method of detecting an analyte. An addressable location of the biochip as described above is contacted with a sample that contains at least one analyte. The analyte can be a biological substance, such as those described herein, which adsorbs to (i.e., is captured at) the addressable location. The present method thus accommodates the detection of a plurality of analytes contained in a single sample, each analyte being bound to a unique location on the biochip.

The biochip is then preferably washed with an eluant as described above to remove unbound materials. In this context, the introduction of eluant to small diameter spots of the chromatographic material is best accomplished by a microfluidics process.

Detection of analytes that remain bound to the biochip can be accomplished by a variety of methods. These include microscopy and other optical techniques, mass spectrometry, and electrical techniques. Light-based detection parameters include, for example, absorbance, reflectance, transmittance, birefringence, refractive index, and diffraction measurement techniques.

Fluorescence detection of labeled analytes is particularly popular. Methods involving fluorescence include direct and indirect fluorescent measurement. Specific methods include, for example, fluorescent tagging in immunological methods such as ELISA or sandwich assay.

Other useful techniques include, for example, surface plasmon resonance, ellipsometry, resonant mirror techniques, grating coupled waveguide techniques, multipolar resonance spectroscopy, impedimetric detection, chemiluminescence detection, and electrical conductivity/reduction-oxidation methods. Methods of desorbing and/or ionizing analytes from biochips for direct analysis are well known in the art, and are generally described, for example, in U.S. Pat. No. 6,225,047.

A particularly preferred method of analysis is Surface-Enhanced Laser Desorption/Ionization ("SELDI"), which is described in, for example, U.S. Pat. Nos. 5,719,060 and 6,255,047. In SELDI, an addressable location on the biochip is presented to an energy source such as a laser, which desorbs and ionizes the analyte bound at the addressable location. The ionized analyte is then detected directly in a time-of-flight ("TOF") mass spectrometer, for example, thereby yielding the mass-to-charge ratio of the desorbed analyte. By repeatedly shifting and positioning the biochip within the probe interface to align with the laser, each addressable location on the biochip can be similarly analyzed.

Additionally, an ion mobility spectrometer can be used to analyze samples. The principle of ion mobility spectrometry is based on different mobility of ions. Specifically, ions of a sample produced by ionization move at different rates, due to their difference in, e.g., mass, charge, or shape, through a tube under the influence of an electric field. The ions, which are typically in the form of a current, are registered at the detector which can then be used to identify the sample. One advantage of ion mobility spectrometry is that it can operate at atmospheric pressure.

Furthermore, a total ion current measuring device can be used to analyze samples. This device can be used when the probe has a surface chemistry that allows only a single class of analytes to be bound. When a single class of analytes is bound on the probe, the total current generated from the ionized analyte reflects the nature of the analyte. The total ion current from the analyte can then be compared to stored total ion current of known compounds. Therefore, the identity of the analyte bound on the probe can be determined.

An advantage of the biochips and analytical method of this invention is that binding and detecting analytes are effective in picomolar or even attomolar amounts of analyte. In accordance with the teachings of this invention, it is thus possible to discover certain subclasses of biological substances referred to as biomarkers. In the present context, a biomarker is an organic biological substance, particularly a polypeptide or protein, which is differentially present in a sample taken from a diseased subject as compared to a sample taken from a healthy subject. A biomarker is differentially present in samples taken from diseased subjects if it is present at an elevated level or a decreased level relative to the level present in a sample taken from a healthy subject. The chromatographic material of the present invention, particularly in the form of a biochip, allows the rapid discovery and identification of biomarkers.

This method is useful for protein profiling, in which proteins in a sample are captured using one or more different chromatographic materials of this invention and then the captured analytes are detected. In turn, protein profiling is useful for difference mapping, in which the protein profiles of different samples are compared to detect differences in protein expression between the samples.

The following examples are given to illustrate the present invention. It should be understood, however, that the invention is not to be limited to the specific conditions or details described in these examples. All references to publicly available documents, including patents, are incorporated herein by reference as if set forth fully in their entireties.

Example 1

Preparation of a Dimethylaminopropyl Thiol Derivative of Cellulose 100 ml of cellulose beads were washed extensively with 1M sodium hydroxide solution and then with water until neutral pH was obtained. To the drained beads were added 18 ml of 0.5 M sodium hydroxide and 10 ml of allylbromide. The resultant mixture was then stirred vigorously overnight at room temperature.

The beads were washed with water to remove by-products, yielding allyl-cellulose for a substrate for the attachment of various functionalities.

The beads of allyl-cellulose were condensed with 25 g of dimethylaminopropylthiol to give the material as shown below:

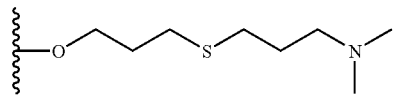

The product resin exhibited a dimethylamino moiety density of 150 μmol/mL of resin. Binding capacity for bovine albumin at physiological ionic strength and pH 8.6 was 39 mg/mL.

Example 2

Preparation of a Dimethylaminoethyl Thiol Derivative of Cellulose 100 mL of allyl cellulose beads, obtained according to the protocol described above in example 1, were condensed with 25 g of dimethylaminoethylthiol to give the following material:

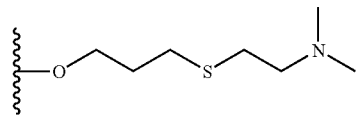

The product exhibited a dimethylamino moiety density of 87 μmol/mL of resin. The binding capacity for bovine albumin at physiological ionic strength and pH 8.6 was 21 mg/mL. The terminal dimethylamino moiety was quaternized by the addition of diethylaminoethyl chloride at pH 12 for 6 hours to give a derivative, which exhibited a binding capacity of the resin reached 27 mg of albumin per mL.

Example 3

Coupling of Dimethylaminopropylamine to an Allylated Solid Support 100 mL of allyl cellulose beads obtained according to the protocol described above in example 1 were condensed with 25 g of dimethylaminopropylamine to give the following material:

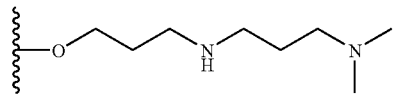

The product exhibited a dimethylamino moiety density of 126 μmol/mL of resin. The binding capacity for bovine albumin at physiological ionic strength and pH 8.6 was 38 mg/mL.

Example 4

Preparation of a Dimethylaminoethylamine Derivative of Cellulose 100 mL of allyl cellulose beads obtained according to the protocol described above in example 1 were first condensed with 25 g of thiohexanoic acid and. The resultant carboxyl derivative was then condensed with dimethylaminoethylamine, using EEDQ as a condensation agent, to give the following product:

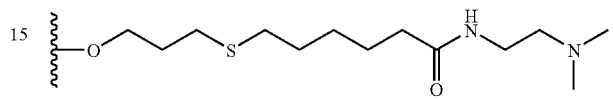

The product exhibited a dimethylamino moiety density of 95 μmol/mL of resin. The binding capacity for bovine albumin at physiological ionic strength and pH 8.6 was 35 mg/mL.

Example 5

Preparation of a Thiocholine Derivative of Cellulose 100 mL of allyl cellulose beads obtained according to the protocol described above in example 1 were condensed with 20 g of thiocholine to give the following product:

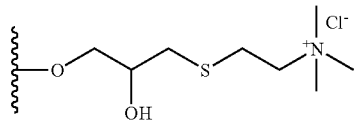

The product exhibited a trimethylammonium moiety density of 86 μmol/mL of resin. The binding capacity for bovine albumin at physiological ionic strength and pH 8.6 was 22 mg/mL.

Example 6

Preparation of a Dimethylaminopropylamine Derivative of Cellulose 100 mL of allyl cellulose beads obtained according to the protocol described above in example 1 were first condensed with 25 g of thiohexanoic acid. The resultant carboxyl derivative was reacted with dimethylaminopropylamine, using EEDQ as a condensation agent to give the following product:

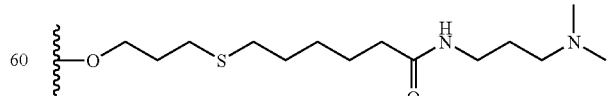

The product exhibited a dimethylamino moiety density of 70 μmol/mL of resin. The binding capacity for bovine albumin at physiological ionic strength and pH 8.6 was 13 mg/mL.

Example 7

Preparation of a Phenyl Ethyl Derivative of Cellulose 100 ml of cellulose beads were washed extensively with 1M sodium hydroxide solution and then with water until neutral pH was obtained. To the drained beads were added 18 ml of 0.5 M sodium hydroxide and 10 ml of allylbromide. The resultant mixture was then stirred vigorously overnight at room temperature.

The beads were washed with water to remove by-products, yielding allyl-cellulose for a substrate for the attachment of various functionalities.

The allyl-cellulose beads were brominated by the addition of potassium bromide and N-bromosuccinimide under acidic conditions and then mixed with 5 g of phenylethyl mercaptan to give the following product:

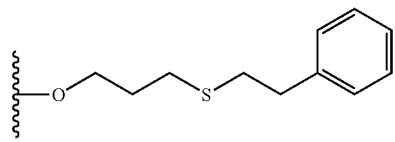

The product exhibited a phenylethyl moiety density of about 50 μmol/mL of settled beads. The binding capacity for bovine albumin at physiological ionic strength and pH 7 was 27 mg/mL. By contrast, a commercially available phenyl derivative for HIC chromatography (Phenyl Sepharose) gave a binding capacity of 2 mg/mL.

Example 8

Preparation of an Phenyl-Propyl Hydrophobic Derivative of Cellulose 100 mL of allyl-cellulose beads as prepared according to example 7 were brominated by addition of potassium bromide and N-bromosuccinimide in acidic conditions and then mixed with 6 mL of phenyl-propyl-amine to give the following product:

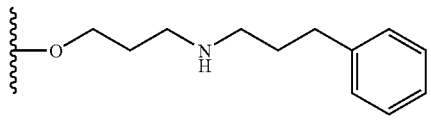

The product exhibited a phenylpropyl moiety density of about 50 μmol/mL of settled beads. The binding capacity for bovine albumin at physiological ionic strength and pH 7 was of 45 mg/mL.

Example 9

Preparation of an Aliphatic Hydrophobic Derivative of Cellulose 100 ml of allyl-cellulose beads prepared according to example 7 were brominated by the addition of potassium bromide and N-bromosuccinimide under acidic conditions and then mixed with 6 mL of hexylamine-amine to give the following product:

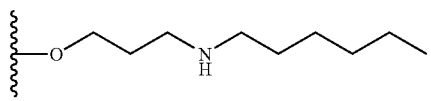

The product exhibited a hexylamino moiety density of about 55 μmol/mL of settled beads. The binding capacity for bovine albumin at physiological f ionic strength and pH 7 was 47 mg/mL. By contrast, a similar product obtained using glucamine (a hydrophilic ligand) instead of hexylamine gave a binding capacity of 4 mg/mL.

Example 10

Preparation of an Octanol Hydrophobic Derivative of Cellulose 100 ml of allyl-cellulose beads prepared according to example 7 were brominated by the addition of potassium bromide and N-bromosuccinimide under acidic conditions and then mixed with 6 mL of 1,8-thiooctanol to give the following product:

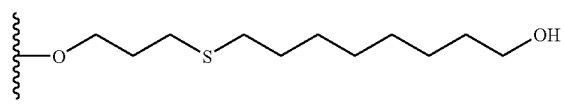

The product exhibited an octanol moiety density more than 50 μmol/mL of settled beads. The binding capacity for bovine albumin at physiological ionic strength and pH 7 was higher than 40 mg/mL.

Example 11

Preparation of an Phenyl-Propyl Hydrophobic Derivative of Zirconia Composite Beads 50 ml of zirconia porous beads that were filled with an agarose gel (6% by volume) were allylated using a similar protocol as the one described in example 7 using 2 mL allyl-bromide and 2 mL 1 M sodium hydroxide. The resultant allylated zirconia composite beads were washed extensively with water to eliminate by-products and until neutral pH was obtained.

The allyl-derivative was brominated by the addition of potassium bromide and N-bromosuccinimide under acidic conditions and then mixed with 6 mL of phenyl-propyl-amine.

The product exhibited a phenylpropyl moiety density of about 60 μmol/mL of settled beads. The binding capacity for bovine albumin at physiological ionic strength and pH 7 was 30 mg/mL.

We claim:
1. A chromatographic material comprising:
   (a) a terminal binding functionality;
   (b) a hydrophobic linker comprising at least one functionality that is different from the terminal binding functionality; and
   (c) a solid support,
   wherein
   the hydrophobic linker links the terminal binding functionality to the solid support; and the chromato- graphic material is capable of binding bovine albumin at physiological ionic strength, wherein the chromatographic material

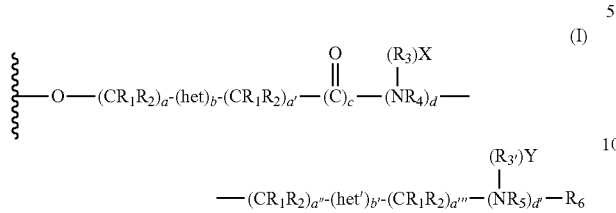

wherein
each of $R_1$, $R_2$, and $R_4$, is H
$R_6$ is $C_{6-alkyl}$;
$R_3$ and $R_{3'}$, together with X and Y, respectively, are absent;
a is 3;
a', a", and a'" are all 0;
b and b' are both 0;
c is 0;
d is 1;
d' is 0; and
the wavy line represents the solid support.

2. A chromatographic material comprising:
(a) a terminal binding functionality;
(b) a hydrophobic linker comprising at least one functionality that is different from the terminal binding functionality; and
(c) a solid support,
wherein
the hydrophobic linker links the terminal binding functionality to the solid support; and the chromatographic material is capable of binding bovine albumin at physiological ionic strength, wherein the chromatographic material has a formula selected from the group consisting of:

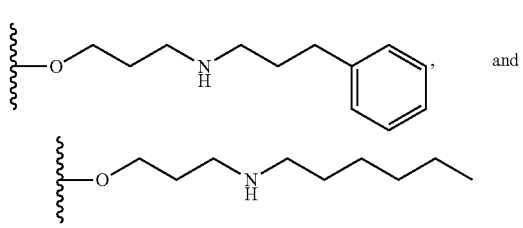

3. The chromatographic material according to claim 1, wherein the solid support is an organic material.

4. The chromatographic material according to claim 3, wherein the organic material is one selected from the group consisting of cellulose, agarose, dextran, polyacrylates, polystyrene, polyacrylamide, polymethacrylamide, copolymers of styrene and divinylbenzene, and mixtures thereof.

5. The chromatographic material according to claim 1, wherein the solid support is in the form of a bead or particle.

6. The chromatographic material according to claim 2, wherein the solid support represented by the wavy line is in the form of a bead or particle.

7. The chromatographic material according to claim 2, wherein the solid support represented by the wavy line is an organic material and the organic material is one selected from the group consisting of cellulose, agarose, dextran, polyacrylates, polystyrene, polyacrylamide, polymethacrylamide, copolymers of styrene and divinylbenzene, and mixtures thereof.

* * * * *